United States Patent [19]

Woell

[11] Patent Number: 5,017,726

[45] Date of Patent: May 21, 1991

[54] PROCESSES FOR THE CONVERSION OF MYRCENE TO NEROL AND CITRAL

[75] Inventor: James B. Woell, Lawrenceville, N.J.

[73] Assignee: Union Camp Corporation, Princeton, N.J.

[21] Appl. No.: 269,278

[22] Filed: Nov. 9, 1988

[51] Int. Cl.$^5$ ............................................ C07C 47/02
[52] U.S. Cl. .................................................. 568/448
[58] Field of Search ........................................ 568/448

[56] References Cited

U.S. PATENT DOCUMENTS

| | | | |
|---|---|---|---|
| 3,382,276 | 5/1968 | Schenck | 568/448 |
| 3,493,619 | 2/1970 | Marbet | 568/448 |
| 4,226,744 | 10/1980 | Näf | 568/448 |

FOREIGN PATENT DOCUMENTS 0021074  1/1981  European Pat. Off. ............ 568/448

*Primary Examiner*—Werren B. Lone
*Attorney, Agent, or Firm*—Edward J. Sites

[57] ABSTRACT

A novel process for converting myrcene to a key palladium-myrcene complex using palladium (II) chloride in the presence of an aqueous cycloamide solvent and lithium salt is disclosed. Novel processes for converting the palladium-myrcene complex to citral using a phosphine compound, or to nerol using a nitrogen-donor compound in the presence of hydrogen gas, are also presented.

45 Claims, No Drawings

PROCESSES FOR THE CONVERSION OF MYRCENE TO NEROL AND CITRAL

BACKGROUND OF THE INVENTION

Oxygenated derivatives of monoterpenes, such as nerol and citral, are of great importance to a number of industries. Although some processes for their commercial production are available, new and/or better synthetic routes are needed.

The application of organometallic chemistry to monoterpene transformation has been the subject of a number of studies. Early experiments are reported in McQuillin et al., *J. Chem. Soc. Perkin Trans. I*, pp. 809–815 (1974), and Dunne et al., *J. Chem. Soc. (C)*. pp. 2196–2200, 2200–2203, and 2203–2206 (1970). In these studies, the authors prepared several allyl palladium complexes of terpene compounds, including those resulting from the reaction of palladium with myrcene. Cyclization of myrcene, however, was found to be a problem, and neither nerol nor citral resulted from the described processes.

Building on the earlier work of these authors, Takahashi et al., *Journal of Organometallic Chemistry*, Vol. 266, pp. 327–336 (1984) successfully prepared a mixture of citral and nerol utilizing a two-step method. First, myrcene was reacted with dichlorobis(acetonitrile)palladium in the solvent hexamethylphosphoric triamide (HMPA) or in the presence of a base such as $Li_2CO_3$ using dimethylformamide (DMF) as solvent, to yield a non-cyclized palladium-myrcene complex. Although the reported yield of the palladium-myrcene complex in the HMPA process was relatively good, the complex formation in the $Li_2CO_3$/DMF process was somewhat low, approximately 33%. In the second step of the reported process, the complex was isolated, and then treated with base to yield terpene aldehydes and alcohols such as citral and nerol. One major drawback of these processes, however, is that they necessitate two steps, requiring isolation of the intermediate before further processing. Moreover, the product obtained using these methods is a mixture of both citral and nerol. Furthermore, these reactions have the additional disadvantage of a temperature limitation, since at high temperatures the solvents HMPA and DMF are decomposed by palladium species. See Bombieri et al., *Inorganica Chimica Acta*, Vol. 86, pp. 121–125 (1984); Fahey et al., *Journal of Organic Chemistry*, Vol. 39, pp. 3276–77 (1974). Finally, the use of HMPA in any process is undesirable, since HMPA is an extremely potent toxin, as well as a suspected carcinogen.

Nerol and citral are compounds of high significance to the flavor, fragrance and synthetic vitamin industries. Additional and/or better processes for their commercial production, particularly processes employing the readily available starting material myrcene, are needed. The present invention is directed to this important end.

SUMMARY OF THE INVENTION

The present invention provides a novel process for producing a palladium-myrcene complex of the formula

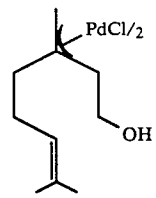

comprising contacting myrcene with palladium (II) chloride in the presence of an aqueous cycloamide solvent and a lithium salt. The complex thus formed provides a key intermediate for further conversion to the important compounds citral and nerol. The subject invention also encompasses novel methods for carrying out such conversions.

In accordance with the present invention, citral may be produced by a novel process in which a palladium-myrcene complex of the formula

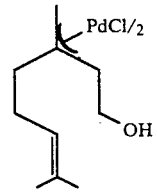

is contacted with a phosphine compound. The present invention further provides a novel process for producing nerol comprising contacting a palladium-myrcene complex of the formula

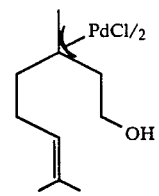

with a nitrogen-donor compound in the presence of hydrogen gas.

DETAILED DESCRIPTION OF THE INVENTION

The subject invention involves, in one aspect, the production of a key palladium-myrcene complex. This key complex provides an intermediate for further reaction to citral (that is, 3,7-dimethyl-(E,Z)-2,6-octadienal) and nerol (that is, 3,7-dimethyl-(Z)-2,6-octadien-1-ol), compounds of significant importance to the flavor, fragrance and synthetic vitamin industries. Specifically, the present invention provides a process for producing a palladium-myrcene complex of the formula

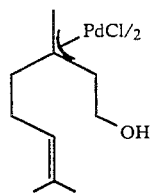

comprising contacting myrcene with a palladium (II) chloride in the presence of an aqueous cycloamide solvent and a lithium salt.

The myrcene employed in the subject processes may be pure myrcene or other suitable mixtures of compounds containing myrcene, as will be apparent to those skilled in the art. One readily available and relatively inexpensive source of myrcene is a myrcene and limonene mixture in a ratio of about 80 to about 20, respectively, a product which is commercially available from various sources, including Union Camp Corporation, Wayne, New Jersey.

The palladium (II) chloride may be added directly as $PdCl_2$. Alternatively, it may be formed in situ by the addition of a source of chloride ion, such as LiCl or NaCl, to a palladium (II) salt, such as $PdSO_4$, $Pd(NO_3)_2$, $Pd_3(PO_4)_2$ and $Pd(BF_4)_2$. Other sources of chloride ion and palladium (II) salts suitable for in situ generation of the palladium (II) chloride will be apparent to those skilled in the art. In generating the palladium (II) chloride in situ, the chloride ion source and the palladium (II) salt may be added in varying ratios of $Pd^{+2}$ to $Cl^-$, including 2:1 and 1:1. If desired, the $PdCl_2$ compound may be complexed with loosely coordinated ligand donors, such as acetonitrile, benzonitrile, 1,5-cyclooctadiene and dimethyl sulfoxide. Thus, the palladium (II) salt may be in the form of, for example, dichlorobisacetonitrile palladium, that is, $PdCl_2(CH_3CN)_2$. Other suitable ligand donors for coordination with the $PdCl_2$ compound will be apparent to those skilled in the art. These and other obvious variations are intended to be within the ambit of the phrase palladium (II) chloride, as used herein. Preferably, the palladium (II) chloride is $PdCl_2$ or $PdCl_2(CH_3CN)_2$.

Suitable aqueous cycloamide solvents include substituted and unsubstituted pyrrolidones, such as N-methylpyrrolidone, substituted and unsubstituted imidazolidinones, and substituted and unsubstituted pyrimidones. Other suitable aqueous cycloamide solvents will be apparent to those skilled in the art. Preferably, the aqueous cycloamide solvent is aqueous N-methylpyrrolidone, a compound of the formula

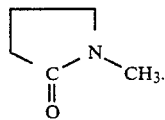

Not only does aqueous N-methylpyrrolidone promote appropriate and efficient complexation of myrcene and palladium (II) chloride, it also lacks the toxic and carcinogenic properties found in HMPA. N-methylpyrrolidone is also less prone to decomposition by palladium than DMF.

Examples of lithium salts suitable for use with the present invention include, but are not limited to, $Li_3PO_4$, $Li_2B_4O_7$, $Li_2CrO_4$, $Li_2SO_4$, $LiNO_3$, $Li_2WO_4$, and $Li_2CO_3$. Other suitable lithium salts will be apparent to those skilled in the art. Preferably, the lithium salts are selected from the group consisting of $Li_3PO_4$, $Li_2B_4O_7$, $Li_2CrO_4$, $Li_2SO_4$, $Li_2WO_4$, $Li_2MoO_4$, and $Li_2CO_3$. Most preferably, the lithium salt is $Li_2B_4O_7$ and $Li_2SO_4$. $LiN_3$ is least preferred in that it forms only a relatively small amount of the desired palladium-myrcene complex. As one skilled in the art will recognize, such salts may, if desired, be formed in situ.

The palladium-myrcene complex-forming reaction proceeds best at or above room temperature. Elevating the temperature results in increased reaction rates. Most preferably, the reaction is carried out at temperatures ranging from room temperature to 70° C. The reaction may be conducted at atmospheric pressure, and generally runs to completion within a few hours. To maximize yields, continual stirring by manual or mechanical means may be employed. Ultrasound may also be used in conjunction with, or in place of, the continual stirring.

The palladium-myrcene complex thus formed provides a suitable intermediate for the production of nerol or citral, and the present invention also includes processes for producing these important compounds. Such processes, which are described in detail below, provide high yields of the desired product, nerol or citral, as the case may be. Moreover, the citral process results in citral product, substantially free of nerol, and similarly, the nerol process results in a nerol product, substantially free of citral.

Thus, the present invention further contemplates a process for producing citral in high yields substantially free of nerol, comprising contacting a palladium-myrcene complex of the formula

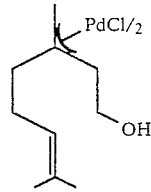

with a phosphine compound.

Surprisingly, the phosphine compound acts to stabilize an otherwise unstable citral end product to both the palladium metal and the thermal conditions of the subject reaction process. Suitable phosphine compounds include, but are not limited to, $PR_1R_2R_3$ wherein $R_1$, $R_2$ and $R_3$ are the same or different and each represents a substituted or unsubstituted $C_1$–$C_{20}$ alkyl, substituted or unsubstituted $C_2$–$C_{20}$ alkenyl, substituted or unsubstituted $C_2$–$C_{20}$ alkynyl, or substituted or unsubstituted $C_6$–$C_{20}$ aryl. Other suitable phosphine compounds will be apparent to those skilled in the art. Preferred phosphine compounds are $PR_1R_2R_3$ wherein $R_1$, $R_2$ and/or $R_3$ are substituted or unsubstituted phenyl. Preferred phosphine compounds are where $R_1$, $R_2$ and/or $R_3$ are unsubstituted phenyl or para-substituted trifluoromethylphenyl. If desired, the phosphine compounds may be supported on a suitable support material. As those skilled in the art will recognize, providing supported phosphine compounds will result in easier separation and recovery of the palladium species. Such support materials are conventional and include polymeric and inorganic materials. An example of a suitable polymeric material is polystyrene cross-linked with divinyl benzene. A preferred embodiment includes $PR_1R_2R_3$ wherein $R_1$, $R_2$ and/or $R_3$ are phenyl and wherein said $PR_1R_2R_3$ is supported on polymeric polystyrene cross-linked with divinyl benzene, a commercially available product from Aldrich Chemical Company, Milwaukee, Wisconsin. Other polymeric and inorganic materials suitable for supporting the phosphine compounds for use in the subject process will be apparent to those skilled in the art.

The citral-producing reaction proceeds best in temperatures of about 110° C.

The palladium-myrcene complex employed in the novel process can be obtained by using methods known to those skilled in the art, such as the methods disclosed in Takahashi et al., *Journal of Organometallic Chemistry*, Vol. 266, pp. 327-336 (1984). Alternatively, the novel methods disclosed herein may be employed to obtain the palladium-myrcene complex utilized in the subject process.

The palladium-myrcene complex may be first isolated, and then contacted with the phosphine compound to yield citral. Accordingly, the present invention also encompasses a process for producing citral comprising: (i) contacting myrcene with palladium (II) chloride in the presence of an aqueous cycloamide solvent and a lithium salt to form a palladium-myrcene complex of the formula

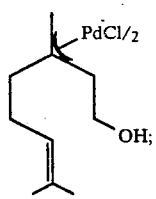

(ii) isolating the resultant palladium-myrcene complex; and (iii) contacting the isolated palladium-myrcene complex with a phosphine compound. Suitable techniques for isolating the palladium-myrcene complex will be readily apparent to those skilled in the art, and include techniques such as the column chromatography procedures set forth in Takahashi et al., *Journal of Organometallic Chemistry*, Vol. 266, pp. 327-336 (1984).

Surprisingly, it has also been found that the palladium-myrcene complex need not be isolated prior to contacting with the phosphine compound, thereby providing a "one-pot" process. Moreover, it has been surprisingly discovered that the palladium-myrcene complex-forming, and the citral-forming reactions need not be carried out in a two-step fashion. Instead, the phosphine compound may be added directly to the myrcene along with the palladium-myrcene complex forming reagents, to yield, in one step, the desired citral product. Thus, an additional aspect of the invention involves a process for producing citral comprising contacting myrcene with: (i) palladium (II) chloride in the presence of an aqueous cycloamide solvent and a lithium salt; and (ii) a phosphine compound. Reagents (i) and (ii) can be added in step-wise order, that is, reagents (i) first, and then reagent (ii), or alternatively, reagents (i) and (ii) can be added simultaneously. When reagents (i) and (ii) are added simultaneously, the best results are achieved where the ratio of $Pd^{+2}$ to $Cl^-$ is 1 to 1. For maximum yields, at least step (ii) in these reactions should be carried out at about 100° C. to about 140° C., most preferably at about 110° C.

The foregoing discoveries clearly provide an efficient and commercially viable pathway to the important compound citral.

A further aspect of the present invention involves a process for producing nerol in high yields and substantially free of citral, comprising contacting a palladium-myrcene complex of the formula

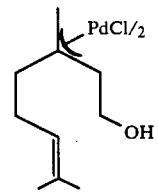

with a nitrogen-donor compound in the presence of hydrogen gas. Suitable nitrogen-donor compounds include, but are not limited to, unsubstituted pyridine, substituted pyridines such as 2-methyl- pyridine and 2-phenyl-pyridine, pyridine-N-oxide, triethylamine and N,N-diethyl-aniline. Preferably, the nitrogen-donor compounds are selected from 2-substituted pyridines such as 2-methyl-pyridine and 2-phenyl-pyridine. Most preferably, the nitrogen donor compound is 2-methyl-pyridine.

Preferably, the reaction is carried out at room temperature and at a hydrogen gas pressure of three atmospheres, although other temperatures and pressures may also be employed.

The palladium-myrcene complex utilized in the novel nerol-producing process can be obtained by using methods known to those skilled in the art, such as the methods disclosed in Takahashi et al., *Journal of Organometallic Chemistry*, Vol. 266, pp. 326-336 (1984). Alternatively, the novel methods disclosed herein may be employed to obtain the palladium-myrcene complex utilized in the subject process.

The palladium-myrcene complex may be first isolated, and then contacted with the nitrogen-donor compound in the presence of hydrogen gas. Accordingly, the present invention also encompasses a process for producing nerol comprising: (i) contacting myrcene with palladium (II) chloride in the presence of an aqueous amide solvent and a lithium salt to form a palladium-myrcene complex of the formula

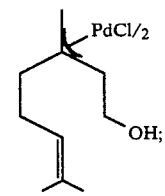

(ii) isolating the resultant palladium-myrcene complex; and (iii) contacting the isolated palladium-myrcene complex with a nitrogen-donor compound in the presence of hydrogen gas. Suitable techniques for isolating the palladium-myrcene complex will be readily apparent to those skilled in the art, and include techniques such as the column chromatography procedures set forth in Takahashi, et al., *Journal of Organometallic Chemistry*, Vol. 266, pp. 327–336 (1984).

Alternatively, the palladium-myrcene need not be isolated prior t contacting with the nitrogen-donor compound and the hydrogen gas, thereby providing a "one pot" process.

Accordingly, an additional aspect of the invention involves a process for producing nerol comprising contacting myrcene with, in order, (i) palladium (II) chloride in the presence of an aqueous cycloamide solvent and a lithium salt; and (ii) a nitrogen-donor compound in the presence of hydrogen gas. Reagents (i) and (ii) are added in step-wise order, that is, reagents (i) first, and then reagents (ii).

The aforementioned processes clearly provide an efficient and commercially viable pathway to the important compound nerol.

The citral and nerol compounds produced by the subject processes are useful in a variety of ways, for example, they may be employed as a fragrance or a flavor additive or as a precursor for the synthesis of vitamins A and E. See Derfer et al., "Terpenoids", pp. 709–762 in *Kirk-Othmer Encyclopedia of Chemical Technology*, 3rd ed., Vol. 22, Wiley Interscience Publications (New York, 1983), the disclosures of which are incorporated by reference herein.

The present invention is further described in the following Examples. These Examples are not to be construed as limiting the scope of the appended claims.

EXAMPLES

In the Examples which follow, the myrcene employed was a myrcene and limonene mixture in a ratio of about 80 to about 20, respectively.

EXAMPLE 1

Production of a Palladium-Myrcene Complex of the Formula

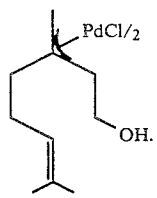

To a solution of N-methylpyrrolidone (25 ml) and $Li_3PO_4$ (1.81 gm) or $Li_2B_4O_7$ (2.61 gm) was added $PdCl_2(CH_3CN)_2$ (1.0101 gm) and water (2.5 ml). The solution was briefly stirred using mechanical stirring, and myrcene (1.7619 gm) was added by pipet. The mixture was then briskly stirred (mechanical stirring) for 5 hours at room temperature, and 50 ml of toluene was added. The organic phase was then dried over $CaCl_2$ overnight in a hood, and separated by column chromatography on florosil gel with toluene/ethyl acetate.

The resulting isolated product was analyzed by NMR and GC. NMR data confirmed the presence of the desired palladium myrcene complex. No cyclized complex was detected. The yield and selectivity results are shown below in Table 1. Yield calculations in all of the Examples are based on the initial level of Pd(II). Selectivity data is based on consumed myrcene. The amount of myrcene remaining was measured by external standard weight percent GC.

TABLE 1

| Process | Yield | Selectivity |
|---|---|---|
| $Li_3PO_4$ N-Methylpyrrolidone Room temperature 5 Hours | 71% | 45% |
| $Li_2B_4O_7$ N-Methylpyrrolidone Room temperature 5 Hours | 73% | 87% |

EXAMPLE 2

Production of Palladium-Myrcene Complex of the Formula

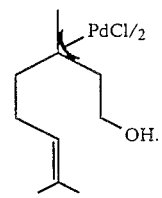

The procedures of Example 1 were substantially followed, except that the reaction was run at about 70° C. for 1.5 hours. The yield and selectivity results are shown in Table 2.

TABLE 2

| Process | Yield | Selectivity |
|---|---|---|
| $Li_3PO_4$ N-Methylpyrrolidone 70° C. 1.5 Hours | 70% | 93% |

EXAMPLE 3

Production of Citral from a Palladium-Myrcene Complex.

To an isolated palladium-myrcene complex (80 mg) of the formula

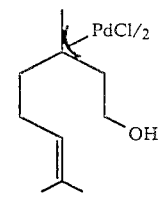

was added toluene (2 ml) and triphenylphosphine (80 mg) in a flask. A water-cooled condenser was placed over the flask and the mixture was heated to about 110° C. for 1.5 hours. The mixture was then cooled to room temperature and 4 ml of tridecane was added. The citral was isolated by distillation and analyzed to confirm the presence of citral. The yield is shown in Table 3.

TABLE 3

| Process | Yield |
|---|---|
| Triphenylphosphine 110° C. 1.5 Hours | 55% |

EXAMPLE 4

Production of Citral from a Palladium-Myrcene Complex.

The procedures of Example 3 were substantially followed, except that the reaction was run at about 140° C. for 2 hours. The yield is shown in Table 4.

TABLE 4

| Process | Yield |
| --- | --- |
| Triphenylphosphine 140° C. 2 Hours | 54% |

EXAMPLE 5

Production of Nerol from a Palladium-Myrcene Complex.

To an isolated palladium-myrcene complex, (40 mg) of the formula

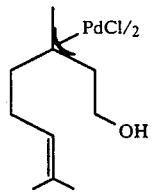

was added toluene (1 ml) and triethylamine (38 μl). The resultant mixture was placed in scintillation vials and a magnetic stirrer added. A balloon containing hydrogen gas at atmospheric pressure was placed over each vial and the mixture was allowed to stir for 20 minutes. The resulting product was analyzed and found to contain nerol. The yield is reported in Table 5.

TABLE 5

| Process | Yield |
| --- | --- |
| Triethylamine $H_2$ Gas Room temperature 20 Mins. | 80% |

EXAMPLE 6

Production of Nerol from a Palladium-Myrcene Complex.

To an isolated palladium-myrcene complex (80 mg) of the formula

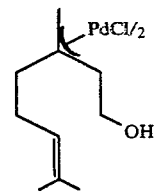

was added toluene (1 ml) and pyridine (0.1 ml). The mixture was placed in a pressure bottle and the bottle placed on a hydrogenator under 50 psi of hydrogen gas pressure. The mixture was shaken for 3 hours. The resulting product was analyzed and found to contain nerol. The yield is reported in Table 6.

TABLE 6

| Process | Yield |
| --- | --- |
| Pyridine $H_2$ Gas Room Temperature 3 Hours | 39% |

EXAMPLE 7

Production of Nerol from a Palladium-Myrcene Complex.

The procedures of Example 6 were substantially followed, except that the nitrogen-containing compound employed was pyridine-N-oxide (100 mg) and the reaction was run for 2 hours. The yield is shown in Table 7.

TABLE 7

| Process | Yield |
| --- | --- |
| Pyridine-N-Oxide $H_2$ Gas Room Temperature 2 Hours | 60% |

EXAMPLE 8

Production of Nerol from a Palladium-Myrcene Complex.

The procedures of Example 6 were substantially followed, except that the nitrogen-containing compound employed was 2-methyl-pyridine (2-picoline) (100 μl) and the reaction was for 2 hours. The yield is shown in Table 8.

TABLE 8

| Process | Yield |
| --- | --- |
| 2-Picoline $H_2$ Gas Room Temperature 2 Hours | 80% |

EXAMPLE 9

Production of Citral from Myrcene (One-Pot/Two-Step).

To a solution of N-methylpyrrolidone (25 ml) and $Li_2B_4O_7$ (1.63 gm) was added $PdCl_2(CH_3CN_2)$ (1.0051 gm) and water (2.5 ml). The solution was briefly stirred, and myrcene (1.7522 gm) was added by pipet. The mixture was then briskly stirred for 5 hours at room temperature, and stored overnight.

To a sample of the solution (0.611 ml) was then added N-methylpyrrolidone (0.889 ml) and triphenylphosphine (0.023 gm). The solution was heated to about 110° C. for 2 hours.

To isolate the citral product, toluene (1.5 ml) was added and the solution washed 5 times with water. The organic phase was then dried by passage through a pipet filled with $K_2CO_3$.

The resulting isolated citral product was analyzed by GC. The yield is shown in Table 9.

TABLE 9

| Process | Yield |
| --- | --- |
| Step 1 | |
| $Li_2B_4O_7$ N-Methylpyrrolidone | N/A* |

TABLE 9-continued

| Process | Yield |
| --- | --- |
| Room Temperature | |
| 5 Hours | |
| Step 2 | |
| Triphenylphosphine | 45% |
| 110° C. | |
| 2 Hours | |

*N/A = not applicable.

EXAMPLE 10

Production of Citral from Myrcene (One-Pot/One-Step).

To a solution of N-methylpyrrolidone (7.5 ml) and $Li_2SO_4$ (0.63 gm) was added $PdSO_4$ (0.2804 gm), LiCl (0.0585 gm), water (0.75 ml) and triphenylphosphine (0.385 gm). The solution was stirred for about ten minutes, and myrcene (0.5201 gm) was added by pipet. The solution was then heated to about 110° C. for 2 hours.

To isolate the citral product from a 0.75 ml aliquot of the reaction mixture, toluene (1.5 ml) was added and the solution washed 5 times with a sodium chloride and water solution. The organic phase was then dried by passage through a pipet filled with $K_2CO_3$.

The resulting isolated product was analyzed by GC. The yield is shown in Table 10.

TABLE 10

| Process | Yield |
| --- | --- |
| $Li_2SO_4$ | 21% |
| N-Methylpyrrolidone | |
| 110° C. | |
| 2 Hours | |

EXAMPLE 11

Production of Citral from Myrcene (One-Pot/One-Step).

To a solution of N-methylpyrrolidone (7.5 ml) and $Li_3PO_4$ (0.55 gm) was added $PdSO_4$ (0.2836 gm), LiCl (0.0554 gm) and triphenylphosphine (0.475 gm) supported on a polymer of polystyrene cross-linked with divinyl benzene. The polymer-supported triphenylphosphine was obtained from Aldrich Chemical Company, Milwaukee, Wisconsin. The solution was stirred for about ten minutes, and myrcene (0.5287 gm) was added by pipet. The solution was then heated to about 110° C. for 2 hours.

The citral product was then isolated and analyzed as in Example 10. The yield is shown in Table 11.

TABLE 11

| Process | Yield |
| --- | --- |
| $Li_3PO_4$ | 16% |
| N-Methylpyrrolidone | |
| 110° C. | |
| 2 Hours | |

Various modifications of the invention in addition to those shown and described herein will be apparent to those skilled in the art from the foregoing description. Such modifications are also intended to fall within the scope of the appended claims.

What is claimed is:

1. A process for producing citral comprising contacting a palladium-myrcene complex of the formula

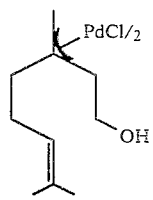

with a phosphine compound of the formula $PR_1R_2R_3$ wherein $R_1$, $R_2$, and $R_3$ are the same or different and each represents a substituted or unsubstituted $C_1$–$C_{20}$ alkyl, $C_2$–$C_{20}$ alkenyl, $C_2$–$C_{20}$ alkynyl or $C_6$–$C_{20}$ aryl.

2. A process according to claim 1 wherein at least one of $R_1$, $R_2$, and $R_3$ are substituted or unsubstituted phenyl.

3. A process according to claim 2 wherein at least one of $R_1$, $R_2$, and $R_3$ are unsubstituted phenyl or para-substituted trifluoromethylphenyl.

4. A process according to claim 1 wherein the phosphine compound is supported on a support material.

5. A process according to claim 4 wherein the support material is polystyrene cross-linked with divinyl benzene.

6. A process according to claim 1 further comprising carrying out the process at a temperature of about 110° C. to about 140° C.

7. A process for producing citral comprising (i) contacting myrcene with palladium (II) chloride in the presence of a substituted aqueous cycloamide solvent and a lithium salt to form a palladium-myrcene complex of the formula

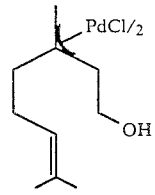

(ii) isolating the resultant palladium-myrcene complex; and (iii) contacting the isolated palladium-myrcene complex with a phosphine compound of the formula $PR_1R_2R_3$ wherein $R_1$, $R_2$, and $R_3$, are the same or different and each represents a substituted or unsubstituted $C_1$–$C_{20}$ alkyl, $C_2$–$C_{20}$ alkenyl, $C_2$–$C_{20}$ alkynyl or $C_6$–$C_{20}$ aryl.

8. A process according to claim 7 wherein the palladium (II) chloride is selected from the group consisting of $PdCl_2$ and $PdCl_2$ loosely coordinated with ligand donors.

9. A process according to claim 8 wherein the ligand donors are selected from the group consisting of acetonitrile, benzonitrile, 1,5-cyclooctadiene and dimethyl sulfoxide.

10. A process according to claim 9 wherein the ligand donors are acetonitrile.

11. A process according to claim 7 wherein the aqueous cycloamide solvent is selected from the group consisting of substituted pyrrolidones, imidazolidinones and pyrimidones.

12. A process according to claim 11 wherein the substituted pyrrolidone is N-methylpyrrolidone.

13. A process according to claim 7 wherein the lithium salt is selected from the group consisting of $Li_3PO_4$, $Li_2B_4O_7$, $Li_2CrO_4$, $Li_2SO_4$, $LiNO_3$, $Li_2WO_4$, $Li_2MoO_4$ and $Li_2CO_3$.

14. A process according to claim 13 wherein the lithium salt is selected from the group consisting of $Li_3PO_4$, $Li_2B_4O_7$, $Li_2CrO_4$, $Li_2SO_4$, $Li_2WO_4$, $Li_2MoO_4$ and $Li_2CO_3$.

15. A process according to claim 14 wherein the lithium salt is selected from the group consisting of $Li_2B_4O_7$ and $Li_2SO_4$.

16. A process according to claim 7 wherein the myrcene is in the form of a myrcene and limonene mixture.

17. A process according to claim 16 wherein the myrcene to limonene ratio is about 80 to about 20.

18. A process according to claim 7 wherein at least one of $R_1$, $R_2$, and $R_3$ is substituted or unsubstituted phenyl.

19. A process according to claim 18 wherein at least one of $R_1$, $R_2$, and $R_3$ is an unsubstituted phenyl or para-substituted trifluoromethylphenyl.

20. A process according to claim 7 wherein the phosphine compound is supported on a support material.

21. A process according to claim 20 wherein the support material is polystyrene cross-linked with divinyl benzene.

22. A process according to claim 7 further comprising carrying out step (i) of the process at a temperature of about room temperature to about 70° C., and carrying out step (iii) of the process at a temperature of about 110° C. to about 140° C.

23. A process according to claim 7 further comprising stirring in step (i) the myrcene, palladium (II) chloride, aqueous cycloamide solvent and lithium salt mixture.

24. A process for producing citral comprising contacting myrcene with: (i) palladium (II) chloride in the presence of an aqueous cycloamide solvent and a lithium salt; and (ii) a phosphine compound of the formula $PR_1R_2R_3$ wherein $R_1$, $R_2$, and $R_3$ are the same or different and each represents a substituted or unsubstituted $C_1$-$C_{20}$ alkyl, $C_2$-$C_{20}$ alkenyl, $C_2$-$C_{20}$ alkynyl or $C_6$-$C_{20}$ aryl.

25. A process according to claim 24 wherein the palladium (II) chloride is selected from the group consisting of $PdCl_2$ and $PdCl_2$ loosely coordinated with ligand donors.

26. A process according to claim 25 wherein the ligand donors are selected from the group consisting of acetonitrile, benzonitrile, 1,5-cyclooctadiene and dimethyl sulfoxide.

27. A process according to claim 26 wherein the ligand donors are acetonitrile.

28. A process according to claim 24 wherein the aqueous cycloamide solvent is selected from the group consisting of substituted pyrrolidones, imidazolidinones and pyrimidones.

29. A process according to claim 28 wherein the substituted pyrrolidone is N-methylpyrrolidone.

30. A process according to claim 24 wherein the lithium salt is selected from the group consisting of $Li_3PO_4$, $Li_2B_4O_7$, $Li_2CrO_4$, $Li_2SO_4$, $LiNO_3$, $Li_2WO_4$, $Li_2MoO_4$ and $Li_2CO_3$.

31. A process according to claim 30 wherein the lithium salt is selected from the group consisting of $Li_3PO_4$, $Li_2B_4O_7$, $Li_2CrO_4$, $Li_2SO_4$, $Li_2WO_4$, $Li_2MoO_4$ and $Li_2CO_3$.

32. A process according to claim 31 wherein the lithium salt is selected from the group consisting of $Li_2B_4O_7$ and $Li_2SO_4$.

33. A process according to claim 24 wherein the myrcene is in the form of a myrcene and limonene mixture.

34. A process according to claim 33 wherein the myrcene to limonene ratio is about 80 to about 20.

35. A process according to claim 24 wherein at least one of $R_1$, $R_2$, and $R_3$ are substituted or unsubstituted phenyl.

36. A process according to claim 35 wherein at least one of $R_1$, $R_2$, and $R_3$ is an unsubstituted phenyl or para-substituted trifluoromethylphenyl.

37. A process according to claim 24 wherein the phosphine compound is supported on a support material.

38. A process according to claim 37 wherein the support material is polystyrene cross-linked with divinyl benzene.

39. A process according to claim 24 wherein step (i) is carried out first, followed by step (ii).

40. A process according to claim 39 further comprising carrying out step (i) of the process at a temperature of about room temperature to about 70° C., and carrying out step (ii) of the process at a temperature of about 110° C. to about 140° C.

41. A process according to claim 39 further comprising stirring in step (i) the myrcene, palladium (II) chloride, aqueous cycloamide solvent and lithium salt mixture.

42. A process according to claim 24 wherein steps (i) and (ii) are carried out simultaneously.

43. A process according to claim 42 wherein the palladium (II) chloride is formed in situ by the addition of a source of chloride ion to a palladium (II) salt in a ratio of $CL^-$ to $Pd^{+2}$ of less than 2:1.

44. A process according to claim 42 further comprising carrying out the process at a temperature of about 100° C. to about 140° C.

45. A process according to claim 42 further comprising stirring the myrcene, palladium (II) chloride, aqueous cycloamide solvent, lithium salt and phosphine compound mixture.

* * * * *